(12) United States Patent
Gollobin

(10) Patent No.: US 6,245,812 B1
(45) Date of Patent: *Jun. 12, 2001

(54) TREATMENT OF HOT FLASHES (FLUSHING) USING LEUCINE ALONE OR IN COMBINATION WITH OTHER BRANCHED CHAIN AMINO ACIDS

(76) Inventor: Charlotte Gollobin, 6710 Bradley Blvd., Bethesda, MD (US) 20817

( * ) Notice: Subject to any disclaimer, the term of this patent is extended or adjusted under 35 U.S.C. 154(b) by 0 days.

This patent is subject to a terminal disclaimer.

(21) Appl. No.: 09/353,768

(22) Filed: Jul. 15, 1999

(51) Int. Cl.⁷ .................................. A61K 31/195
(52) U.S. Cl. ............................................. 514/561
(58) Field of Search ............................. 514/561

(56) References Cited

U.S. PATENT DOCUMENTS

| | | | |
|---|---|---|---|
| 3,608,075 | 9/1971 | Glen et al. | 424/238 |
| 3,733,407 | 5/1973 | Segre | 424/239 |
| 4,315,033 | 2/1982 | Lawrason | 424/319 |
| 4,421,744 | 12/1983 | Gormley | 424/177 |
| 4,687,781 | 8/1987 | Ehrenpreis et al. | 514/557 |
| 4,730,007 | 3/1988 | Ehrenpreis | 514/561 |
| 4,894,373 | 1/1990 | Young | 514/239.2 |
| 5,028,622 | 7/1991 | Plaitakis | 514/561 |
| 5,256,669 | 10/1993 | Askanazi et al. | 514/282 |
| 5,393,784 | 2/1995 | Richardson | 514/561 |
| 5,789,443 | 8/1998 | Gollobin | 516/561 |

OTHER PUBLICATIONS

DiPalma et al., Annu. Rev. Nutr., "Use of Niacin as a Drug", 11:169–87 (1991).
Carpenter, K.J., Experientia Suppl., "The Relationship of Pellagra to Corn and the Low Availability of Niacin in Cereals", 44:197–222, 1983.
Henderson,Ann. Rev. Nutr., "Niacin", 3:289–307, 1983.
Nutrition Reviews, "Pellagragenic Effect of Excess Leucine", vol. 44, No. 1, Jan. 1986, pp. 26–27.
Nutrition Reviews, "Is Leucine Excess a Factor in Pellagra?", vol. 45, No. 10, Oct. 1987, pp. 313–315.
Harper et al., Ann. Rev. Nutr., "Branched–Chain Amino Acid Metabolism", pp. 432,439.
Jacob et al., Present Knowledge in Nutrition, "Niacin", pp. 163–169.
Rao et al., Niacin, "Niacin", pp. 318–331.

Primary Examiner—Russell Travers
Assistant Examiner—Shengjun Wang
(74) Attorney, Agent, or Firm—Jacobson, Price, Holman & Stern, PLLC

(57) ABSTRACT

A method for treating flushing caused by other means than normal estrogen decreases associated with normal or natural menopause. Specifically, the method comprises administering to a patient in need thereof an effective amount of leucine, or leucine in combination with isoleucine, valine and mixtures of isoleucine and valine. Treatment may be achieved via manipulation of dietary protein intake or through direct administration, e.g., dietary supplement or the like. An article of manufacture is also provided.

23 Claims, No Drawings

TREATMENT OF HOT FLASHES (FLUSHING) USING LEUCINE ALONE OR IN COMBINATION WITH OTHER BRANCHED CHAIN AMINO ACIDS

FIELD OF THE INVENTION

This invention is directed to a method for treating hot flashes (flushing) and the like. Specifically, this invention is directed to treatment of flushing and the like caused by means other than the normal reduction of estrogen associated with menopause comprising administering to a patient, an effective amount of leucine. Leucine may be administered by manipulation of diet or in a composition comprising an effective amount of leucine and a pharmaceutically acceptable carrier. A combination of leucine with other branched chain amino acids such as, isoleucine and valine is preferred.

BACKGROUND OF THE INVENTION

Menopausal syndrome consists of a number of varying and often highly distressing symptoms resulting from hormonal imbalance in the female body, specifically a deficiency of estrogen in the body. Symptoms of menopausal syndrome sufficiently severe to require treatment occur in approximately 50 percent of women. One particular symptom experienced by women is hot flashes or flushing. This is characterized by a sudden onset of warmth in the face and neck and often progressing to the chest. Such an episode generally lasts several minutes and is evidenced by a visible red flushing of the skin. Often such episodes are accompanied by sweating, dizziness, nausea, palpitations and diaphoresis.

In U.S. Pat. No. 5,789,443, granted on Aug. 4, 1998, the contents of which are expressly incorporated by reference as if fully set forth herein, the use of leucine either alone or in combination with other branched chain amino acids has been described for the treatment of flushing and the like associated with menopause.

Flushing, however, can be caused by other means than the reduction of estrogen resulting from the onset of natural or normal menopause. "Other means" refers to any causes of human flushing brought on by other than "normal" physical decreases in estrogen associated with normal or natural menopause. In other words, induced menopause can cause flushing. For example, flushing may be induced by certain drug administration. Drugs used to treat breast cancer, such as the anti-estrogens are known to induce flushing. Examples of the anti-estrogens include, but are not limited to, tamoxifen (1-p-β-dimethylamino-ethoxypenyl-trans-1,2-dipheriyl-but-1-ene), and droloxifene ((E)-alpha-(para-(2-(Dimethylamino)ethoxy) phenyl)-alpha'-ethyl-3-s-tilbenol), faslodex (7α-(9-(4,4,5,5,5 -pentafluoropentylsulfinyl) nonyl]estra-1,3,5(10)-triene-3-173-diol), and progestins such as, megestrol (17-Hydroxy-6-methylpregna-3,6-diene-3,20-dione) and medroxyprogesterone ((6alpha)-17-Hydroxy-6-methylpregn-4-ene-3,20-dione). Another class of drugs used in the treatment of breast cancer is the aromatase inhibitors. Examples of the aromatase inhibitors include, but are not limited to, anastrazole (2,2[5-(1H-1,2,4-triazol-1-yl methyl)-1,3-phenylene]bis(2-methylpropiononitrile), fadrozole (4-(5,6,7,8-Tetrahydroimidazo(1,5-a)pyridin-5-yl)benzonitrile), letrozole (4-[1-(cyanophenyl)-1-(1,2,4-triazolyl)methyl] benzonitrile), vorzole (6-((4-chlorophenyl)-(1H-1,2,4-triazol-1-yl)methyl)-1-methyl-1H -benzotriazloe), aminoglutethimide(2-(p-aminophenyl)-2-ethyl -glutarimide), formestane (4-Hydroxyandrostenediona) and exermestane (6-Methyleneandrosta-1,4-diene-3,17-dione).

In the treatment of prostrate carcinoma, lutenizing hormone releasing hormone (LHRH) analogs are administered. Such endocrine therapy suppresses levels of testosterone and is known to cause flushing in about two thirds of the patients undergoing therapy. Examples of LHRH analogs include, but are not limited to, leuprolide acetate and goserelin acetate.

In the treatment of cancer, women subject to powerful drugs may cease menstruating and may experience flushing.

Flushing may be induced as a result of radiation therapy.

Flushing may also be induced by certain surgical procedures. Removal of the testes is known to induce flushing in about half the men receiving such a procedure. Removal of the ovaries is also known to induce flushing in women.

SUMMARY OF THE INVENTION

Flushing induced by other means than associated with menopause can also be successfully treated with leucine in accordance with the teachings of U.S. Pat. No. 5,789,443. Therefore, it is the object of the present invention to provide a method for treating flushing and the like, induced by means other than normal reductions in estrogen associated with normal or natural menopause.

In accordance with a first aspect, the present invention provides a method for the treatment of flushing and the like, by administering to a patient suffering from such symptoms, a therapeutically effective amount of leucine. The treatment of flushing and the like caused by means other than normal reductions in estrogen associated with menopause is envisioned. Preferably, leucine is administered to the patient orally, in combination with other branched chain amino acids such as isoleucine and valine.

In accordance with a second aspect, the present invention provides an article of manufacture which comprises at least one therapeutic composition comprising leucine, effective in the treatment of flushing and the like, and packaging material for containing the at least one therapeutic composition, the packaging material having a label which indicates that the at least one therapeutic composition is therapeutically effective in the treatment of flushing.

DESCRIPTION OF PREFERRED EMBODIMENTS

It is to be understood that while specific embodiments of the present invention are described herein, the invention is not to be limited to such embodiments.

The present invention is directed to the therapeutic use of leucine and/or leucine in combination with branched chain amino acids selected from the group consisting of isoleucine, valine, and mixtures of isoleucine and valine in the general treatment of flushing and the like.

Treatment is directed to flushing caused by any means other than the normal reduction in estrogen associated with normal or natural menopause. Such flushing includes, but is not limited to, drug induced flushing, flushing caused by surgical procedures, and flushing caused by radiation treatment. Some drugs which are known to cause flushing include anti-estrogens, e.g. Tamoxifen (1-p-β-dimethylamino-ethoxypenyl-trans -1,2-diphenyl-but-1-ene) and Droloxifene, and LHRH analogs e.g., leuprolide acetate and goserelin acetate.

The branched chain amino acids of the present invention include leucine, isoleucine and valine. The most preferred forms of these branched chain amino acids include L-leucine, L-isoleucine and L-valine. Due to the depression effect that high intakes of leucine may have on other amino acids in the body, such as valine and isoleucine, it is preferred that isoleucine and valine be administered together with leucine, either as part of the composition or via an alternative route.

The branched chain amino acids according to the present invention may be administered in any form. Further, although any route of administration may be used, the preferred route of administration is orally. Examples of oral forms include both solid and liquid dosage forms, specifically capsules, tablets, dietary supplements, powders, solutions, syrups, elixirs and the like. The branched chain amino acids can also be taken orally administered by manipulation of dietary protein intake.

The therapeutically effective amounts of branched chain amino acids administered is to be an amount sufficient to effectively reduce and/or eliminate flushing and will vary according to the mode of administration and the weight and other characteristics of the patient. Such an effective amount would be easily discernable to a person of ordinary skill in the art. See for example, Remington's Pharmaceutical Sciences, Eighteenth edition, 1990, the disclosure of which is expressly incorporated herein by reference.

The preferred amount of leucine to be administered to the patent is between 250–1000 mg/day, more preferable between 400–700 mg/day. The preferred amount of isoleucine is between 150–700 mg/day, more preferably between 200–500 mg/day. The preferred amount of valine is between 100–600 mg/day, more preferably between 200–400 mg/day. Other compounds may be administered simultaneously with the amino acids, especially where the amino acid is administered in the form of a dietary supplement. Examples of such compounds include, but are not limited to, vitamins, particularly vitamin B6, and minerals, particularly calcium and magnesium. If flushing is drug induced, leucine, which may be administered either alone or in combination with other branched chain amino acids, may be administered simultaneously with the drug which induces the flushing.

Pharmaceutically acceptable carriers, excipients and diluents include those which are well known in the art. Examples of such carriers, diluents and excipients include starch, sugars, talc and the like. Other agents well known in the art may also be included in compositions of the present invention. Examples of such agents include adjuvants, wetting agents, emulsifying agents, and sweetening agents.

The term flushing and the like is intended to mean flushing i.e., a sudden onset of warmth in the face and neck, often progressing to the chest or a visible red flushing of the skin and other frequently accompanying symptoms i.e., often such episodes are accompanied by sweating, dizziness, nausea, palpitations and diaphoresis.

What is claimed is:

1. A method for treating flushing caused by means other than the normal reduction in estrogen associated with normal or natural menopause comprising administering to a patient in need thereof, a therapeutically effective amount of leucine.

2. The method of claim 1, wherein leucine is administered by manipulation of diet.

3. The method of claim 1, wherein leucine is administered in combination with at least one branched chain amino acid.

4. The method of claim 3, wherein the branched chain amino acid is selected from the group consisting of isoleucine, valine and mixtures of isoleucine and valine.

5. The method of claim 3, wherein the combination comprises L-leucine, L-isoleucine and L-valine.

6. The method of claim 1, wherein the therapeutically effective amount of leucine is between 250–1000 mg/day.

7. The method of claim 1, wherein thee therapeutically effective amount of leucine is between 400–700 mg/day.

8. The method of claim 1, further comprising administering isoleucine in an amount between 150–700 mg/day.

9. The method of claim 8, wherein the amount of isoleucine is between 200–500 mg/day.

10. The method of claim 1, further comprising administering valine in an amount between 100–600 mg/day.

11. The method of claim 10, wherein the amount of valine is between 200–400 mg/day.

12. The method of claim 1, wherein leucine is administered in a composition further comprising a pharmaceutically acceptable carrier, diluent or excipient.

13. The method of claim 12, wherein the composition comprises approximately 540 mg of L-leucine, approximately 360 mg L-isoleucine and approximately 300 mg L-valine.

14. The method of claim 12, wherein the composition further comprises vitamin B-6.

15. The method of claim 1, further comprising administering leucine simultaneously with at least one drug which induces flushing.

16. The method of claim 1, wherein flushing is induced by drug therapy.

17. The method of claim 16, wherein the drug therapy comprises treating a patient with at least one, anti-estrogenic drug.

18. The method of claim 17, wherein at least one the anti-estrogenic drug is selected from the group consisting of 1-p-β-dimethylamino-ethoxyphenyl-trans-1,2-diphenylbul-1-ene, (E)-alpha-(par-( 2-(Dimethylamino)ethoxy)phenyl)-alpha'-ethyl-3-s-tilbenol, 7α-(9-(4,4,5,5,5-pentafluoropentylsulfinyl)nonyl]estra-1,3,5(10)-triene-3-17B-diol, 17-Hydroxy-6-methylpregna-3, 6-diene-3, 20-dione and (6alpha)-17-Hydroxy-6-methylpregn-4-ene-3, 20-dione.

19. The method of claim 17, wherein the drug therapy comprises treating a patient with at least one aromatase inhibitor.

20. The method of claim 19, wherein the at least one aromatase inhibitor is selected from the group consisting of 4-(5,6,7,8-Tetrahydroimidazo(1,5-a)pyridin-5-yl) benzonitrile, 4-[1-(cyanophenyl)-1-(1,2,4-triazolyl)methyl] benzonitrile, 6-((4-Chlorophenyl)-(1H-1,2,4-triazol-1-yl) methyl)-1-methyl-1H-benzotriazole, aminoglutethiumide, 4-Hydroxylandrostenedione and 6-Methyleneandrosta-1,4-diene-3,17-dione.

21. The method of claim 16, wherein drug therapy comprises treating a patient with at least one lutenizing hormone releasing hormone (LHRH) analog.

22. The method of claim 21, wherein the at least one LHRH analog is selected from the group consisting of leuprolide acetate and goserelin acetate.

23. The method of claim 1, wherein flushing is caused by surgical procedure.

* * * * *